United States Patent
Albrecht (10) Patent No.: US 8,578,936 B2
(45) Date of Patent: Nov. 12, 2013

(54) SUPPORT FOR SUPPORTING A PATIENT

(75) Inventor: Willi Albrecht, Galgenen (CH)

(73) Assignee: Samarit Medical AG, Zumikon (CH)

( * ) Notice: Subject to any disclaimer, the term of this patent is extended or adjusted under 35 U.S.C. 154(b) by 845 days.

(21) Appl. No.: 12/531,915

(22) PCT Filed: Mar. 19, 2008

(86) PCT No.: PCT/CH2008/000120
§ 371 (c)(1),
(2), (4) Date: Feb. 25, 2010

(87) PCT Pub. No.: WO2008/113200
PCT Pub. Date: Sep. 25, 2008

(65) Prior Publication Data
US 2010/0147313 A1    Jun. 17, 2010

(30) Foreign Application Priority Data
Mar. 20, 2007   (CH) ........................................ 440/07

(51) Int. Cl.
A47B 13/00   (2006.01)
A47B 7/00    (2006.01)
A47C 20/00   (2006.01)
A47C 17/86   (2006.01)
A61F 13/00   (2006.01)
A61F 5/37    (2006.01)
A61F 5/00    (2006.01)
A61G 15/00   (2006.01)
A61B 19/00   (2006.01)

(52) U.S. Cl.
USPC ............ 128/845; 5/601; 5/621; 5/624; 5/630; 5/631; 5/638; 5/640; 5/646; 5/648; 128/846; 128/869; 128/870; 128/872; 128/876; 602/32; 602/33

(58) Field of Classification Search
USPC ............ 5/601, 621, 624, 630, 631, 638, 640, 5/646, 648; 128/846, 869, 870, 872, 876; 602/32, 33
See application file for complete search history.

(56) References Cited

U.S. PATENT DOCUMENTS 2,386,134 A * 10/1945 Mermis ............................. 5/632
(Continued)

FOREIGN PATENT DOCUMENTS

DE    200 09 909 U1   6/2000
(Continued)

OTHER PUBLICATIONS

International Search Report for PCT/CH2008/000120.

*Primary Examiner* — Patricia Bianco
*Assistant Examiner* — Brandon L Jackson
(74) *Attorney, Agent, or Firm* — McCormick, Paulding & Huber LLP (57) ABSTRACT

In order to improve a support (2) for supporting a patient, particularly for surgical procedures in the shoulder region, said support comprising a substantially flat body part (4) and a bowl-shaped head part, said body part (4) comprising a back part (6) and a thorax part (8) tapered in relation thereto, the head part (10) being disposed on said thorax part by means of a transitional region, with the thorax part (8) and the transitional region sloping upwards such that the head part (10) is higher than the back part (6), and with said head part being adapted to the human profile and comprising a removable, inflatable support for adapting the position of the patient to the current positional or treatment requirements, the invention proposes that the transitional region be designed as neck part (12) and also be adapted to the human profile, comprising a removable, inflatable support for adapting the position of the patient to the current positional or treatment requirements.

14 Claims, 5 Drawing Sheets

(56) References Cited

U.S. PATENT DOCUMENTS

| | | | |
|---|---|---|---|
| 4,182,322 A * | 1/1980 | Miller | 5/637 |
| 4,400,820 A * | 8/1983 | O'Dell et al. | 378/209 |
| 4,688,780 A | 8/1987 | Hanz | |
| 5,147,287 A | 9/1992 | Jewell et al. | |
| 5,337,760 A | 8/1994 | Nichols | |
| 5,675,851 A * | 10/1997 | Feathers | 5/632 |
| 6,199,233 B1 * | 3/2001 | Kantrowitz et al. | 5/601 |
| 6,813,788 B2 * | 11/2004 | Dinkler et al. | 5/622 |

FOREIGN PATENT DOCUMENTS

| | | |
|---|---|---|
| WO | 0191642 A1 | 12/2001 |
| WO | 0228338 A2 | 4/2002 |
| WO | 03077821 A1 | 9/2003 |

* cited by examiner

SUPPORT FOR SUPPORTING A PATIENT

CROSS REFERENCE TO RELATED APPLICATIONS

This application claims the priority of Swiss patent application No. 440/07, filed on Mar. 20, 2007 and PCT Application No. PCT/CH2008/000120, filed on Mar. 19, 2008, the disclosures of which are incorporated herein by reference in their entirety.

TECHNICAL FIELD

The invention relates to a support for supporting a patient with a head part and a body part.

PRIOR ART

Numerous rest means are known for operating on or examining patients in the upper body region, for example in the jaw or shoulder region. Rest means of this type can either be incorporated on an appropriate patient couch or be fastened to the patient, for example for a special operation. A typical patient couch with a head part is known from DE 200 09 909 U1 which also proposes providing the head part with a padded cushion part.

However, a common feature of the known positioning aids for patients is the fact that although the head region and the back region of the patient are supported, the neck region is obviously not effectively supported. This is a significant deficiency in the prior art, especially when the patient is anesthetized during the treatment (operation) and for this reason the neck muscles are not tensioned. Furthermore, the lack of support of the patient's neck region has, in particular in operations on the shoulder region in what is known as a beach chair position, proven problematic when the patient has to be moved while under anesthetic. On the one hand, the positioning means according to the prior art can lead to dislocations which post-operatively cause the patient much discomfort. In more severe cases, the absence of effective neck support can even lead to injuries, for example in the vertebral region, if the patient is subjected to sudden movements.

Nevertheless, supporting the neck region gives rise to the problem that the entire unit, which begins at one end—normally somewhat elevated—with a head part and ends at the other end with the back part, must correspond to the body shape of the patient, making the formation of a neck part appear difficult.

SUMMARY OF THE INVENTION

The object of the invention is to propose a support for supporting a patient with a head part and a body part that allows the above-mentioned deficiencies in the prior art to be eliminated and that can be used, in addition, as universally as possible. In any case, a beach chair position should be facilitated for surgical interventions in the shoulder region of the patient. Furthermore, it should be made possible to set, for example when intubating the patient, the change in body position necessary for this purpose.

The object of the invention is achieved by a support for supporting a patient, with a substantially flat body part and a bowl-shaped head part. The body part has a back part and a thorax part which is tapered in relation thereto and on which the head part is arranged by means of a transitional region. The thorax part and the transitional region rise in such a way that the head part is higher than the back part. The head part is adapted to the human profile and has a detachable, inflatable rest for adapting the position of the patient to the positional or treatment requirements. Consequently, the transitional region is embodied as a neck part and is also adapted to the human profile and has a detachable, inflatable rest for adapting the position of the patient to the positional or treatment requirements. In this case, the measures of the invention have in the first place the consequence that the lack of support in the neck region may be made good without this leading to a hard rest having an adverse effect on the neck region. Furthermore, the measures of the invention have the consequence that the entire upper body of the patient rests securely during movements caused by the operator; this is not comprehensively possible in the case of the apparatuses according to the prior art. It has surprisingly been found that the two rest parts for the head and the neck can interact with each other in such a way as to allow specific advantageous changes in head position, for example for intubating the patient, to be brought about. The support allows use in a broad spectrum of positions ranging from the lying-down via the half-sitting-up to the sitting-up beach chair position of the patient.

Advantageously, the dimensions are adapted to the typical human build of patients who are to be operated on or else otherwise treated on a support according to the present invention. For example, the neck part corresponds to the human neck, and the body part is adapted to the human profile. This can lead to different embodiments, if for example a support for children, for adult patients of average weight or for overweight patients is to be manufactured. The rest according to the present invention is particularly advantageous for shoulder operations, the table being erected into what is known as the beach chair position.

For simple manufacture and handling, it may be advantageous if, in the case of the support, at least the back part, the thorax part and the neck part, but preferably also the head part, are embodied in one piece. In order to impart high stability to the support, it may be advantageous for the support to have on the back a reinforcement rail or the like extending substantially in the longitudinal center line.

The patient is fixed to the support. In order to assist this, it is advantageous if the body part has in each of its lateral regions an elongate, slotted recess for fastening a respective belt part of a safety belt. Halves of a safety belt, which are buckled together at the level of the thorax of the patient who is lying on his back, are fastened to this recess. In the region of the body part, the flat support can be placed on an operating table or a similar base. However, it would seem advantageous if means for connecting to an operating table are provided on the head part. These means may advantageously be embodied on the head part as a projection which encircles at least in certain pieces and can be clicked into a corresponding counterpiece embodied or arranged on the operating table. Additionally or alternatively, the support can however also have a support device, which can be attached or detached below the head part, for supporting the head part on an operating table.

Specifically for shoulder operations, it has proven advantageous if the support has support elements which can be attached or detached in the region of the thorax part at both sides. On the one hand, this allows the operator facilitated access to the dorsal shoulder when the support elements are removed and, on the other hand, extended support is ensured, especially when access is not required.

In order to ensure optimum adaptation of various body sizes, the inflatable rest of the head part is embodied in an annular manner. It would also appear advantageous if the inflatable rest of the neck part is embodied in a substantially trapezoidal manner.

It is advantageous if the inflatable rests of the head part and the neck part are detachable, so that they can be supplied in a hygienic manner. It is particularly advantageous if they can be arranged on the head part or on the neck part using a hook-and-loop fastener.

It is advantageous if the detachable, inflatable rest of the head part and /or the detachable, inflatable rest of the neck part has a hook-and-loop fastener which can be used to arrange the rest on the head part or on the neck part of the support. It is also advantageous for use in preparation for, during or after operating if the head part, the neck part and the body part are made predominantly of a plastics material which is transparent to x-rays.

It should be noted in this connection that the terms "back part", "thorax part" and "neck part" denote the approximate position of the human body supported on these elements. The terms are not intended to draw a precise anatomical distinction. On the contrary, the upper region of the back part includes human body parts which still contain the thorax. Furthermore, it is entirely possible for the thorax region of the support to include lower regions of the human neck, in particular those which do not require positioned support by the inflatable rest of the neck region. It should in this case be noted that the dimensions of the human body differ greatly from individual to individual and that a single support according to the present invention is intended to be used and may be used to support humans of different size and weight.

The aforementioned elements and also the elements which are claimed and described in the following exemplary embodiments and are to be used in accordance with the invention are not subject, in their size, configuration, use of material and their technical design, to any particular exceptions, so that the selection criteria known in each field of application may be applied without restriction.

BRIEF DESCRIPTION OF THE DRAWINGS

Exemplary embodiments of the invention will be described hereinafter in greater detail with reference to the drawings, in which.

DESCRIPTION OF THE PREFERRED EMBODIMENTS

The support 2 depicted in FIGS. 1 to 4 for supporting a patient during medical examinations and surgical interventions, in particular during surgical operations in the region of the shoulder region, has a substantially flat body part 4 which is embodied in such a way that a back part 6 merges with a thorax part 8 tapered in relation thereto. The terms "back part" and "thorax part" denote the approximate position of the human body 40 when the body is resting on the support. A head part 10 adjoins the thorax part 8 via a transitional region. In this case, the transitional part is embodied as the neck part 12.

The thorax part 8 has a transitional region 36 which is rounded in relation to the substantially planar back part 6 and by way of which the part of the thorax part 8 that faces the region of transition to the head part 10 is angled upward in relation to the part of the thorax part 8 that faces the back part. As a result, the head part 10 is elevated, when the support 2 rests for example on an operating table 32, by the height h.

The head part 10 is convexly adapted to the typical head shape of an adult human. The edge—apart from in the vicinity of the transitional part—has in the exemplary embodiment described in the present document a projection 28, the purpose of which is to allow the head part, and thus the support, to be connected at least in an adjusted manner—preferably even so as to be able to be clicked-in or locked-in—for example to a known, adjustable head holding part 36 of a known operating table 32.

Figure 1:
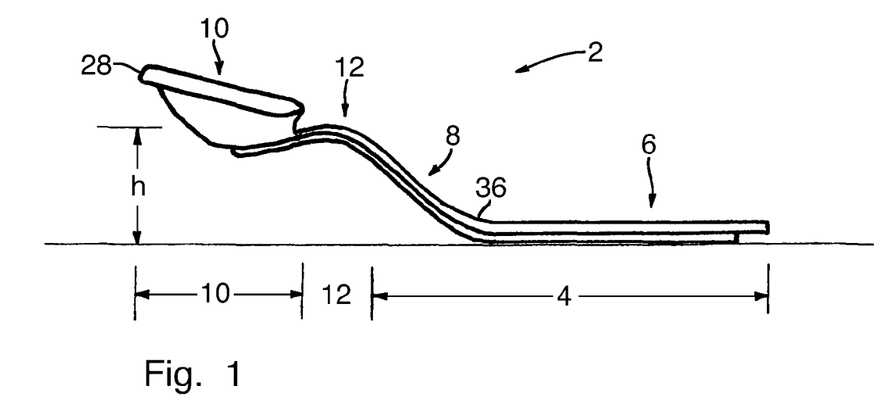
FIG. 1 is a side view of a support which is embodied in one piece according to a first exemplary embodiment of the present invention.
Figure 2:
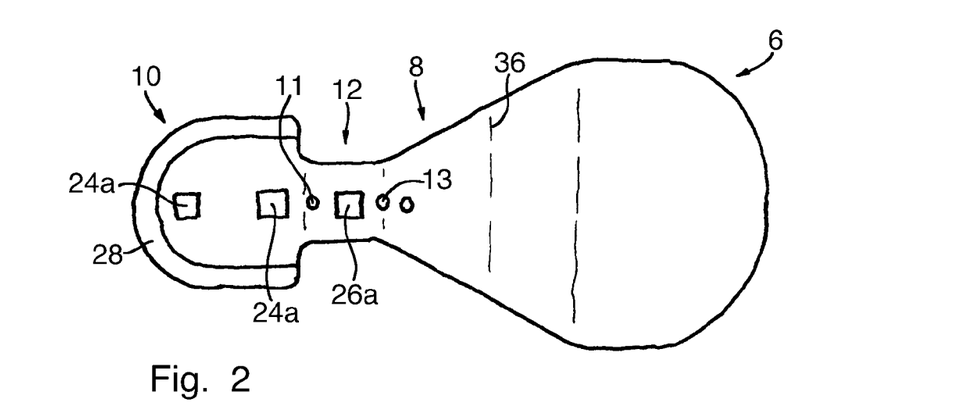
FIG. 2 is a plan view of the support according to FIG. 1.
Figure 3:
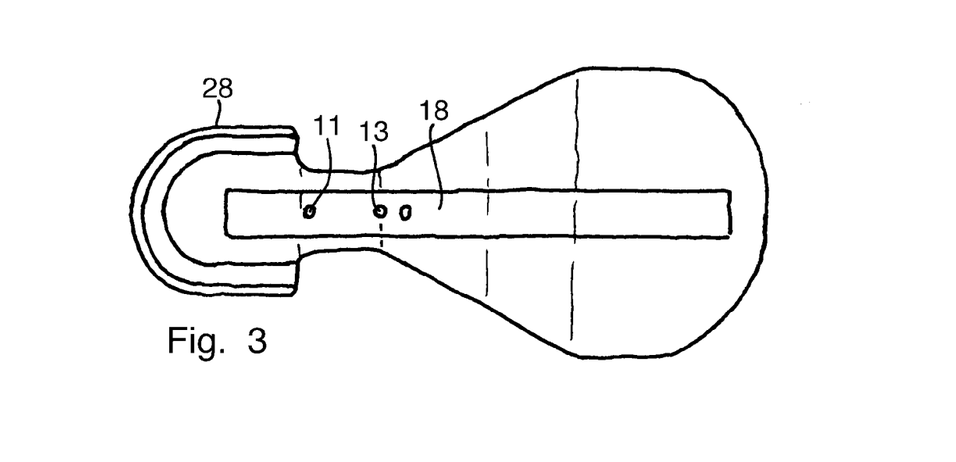
FIG. 3 is a view from below of the support according to FIG. 1.
Figure 4:
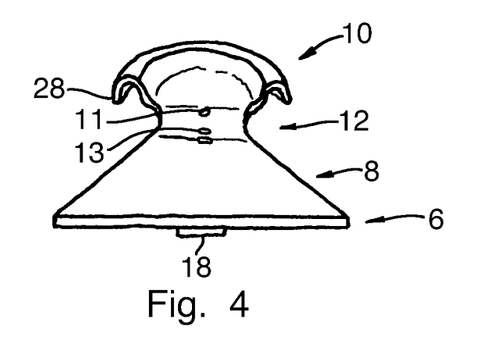
FIG. 4 is a rear view of the support according to FIG. 1.
Figure 5:
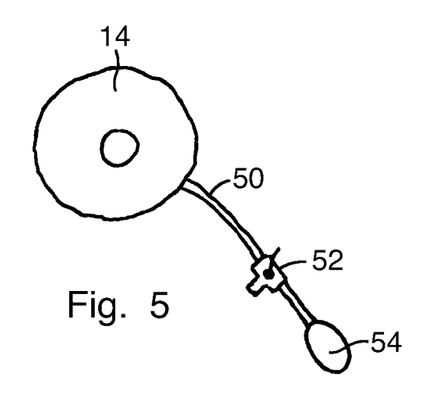
FIG. 5 is a plan view of a rest for the head part of the support according to FIG. 1 with the inflation elements.
Figure 6:
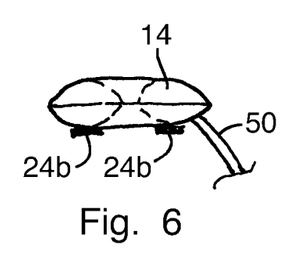
FIG. 6 is a side view of the rest according to FIG. 5.

The head part 10 is in the present exemplary embodiment occupied by an annularly embodied rest part 14 which is arranged on the head part 10 by means of two flat hook-and-loop fasteners 24a and 24b aim I. The rest part 14 is embodied in such a way that the head 42 of a patient can rest on the rest part and the convex shape of the head part serves substantially to secure the position of the head 42 during movements. As illustrated in FIGS. 5 and 6, the rest 14 for the head part 10 is equipped with a tube 50 to be guided through an opening 11 in the support 2, a three-way valve 52 and a hand pump arrangement 54, so that the rest part 14 for the head part 10 can be adapted, before, during and/or after an operation, to the requirements, the head shape and the patient's position and/or the type of treatment.

Figure 7:
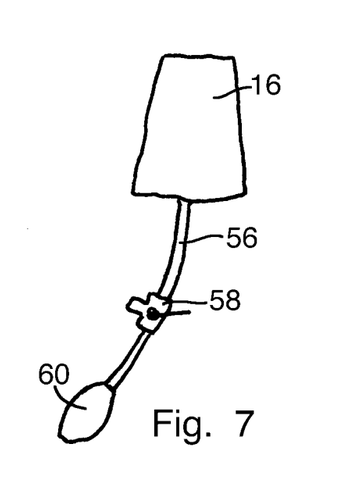
FIG. 7 is a plan view of a rest for the neck part of the support according to FIG. 1 with the inflation elements.
Figure 8:
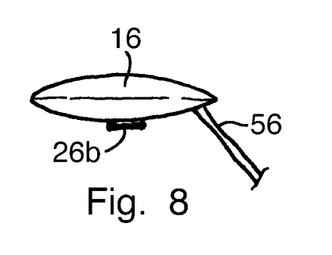
FIG. 8 is a side view of the rest according to FIG. 7.

The neck part 12, which is at the same time also the transition between the body part 4 and the head part 10, is embodied as a surface which is adapted to the typical neck of an adult human. However, this is difficult at least when the patient's position, and thus the position and orientation of his neck 44, cannot be predetermined unambiguously. In order to solve this problem, the neck part 12 is in the present exemplary embodiment also occupied by a preferably trapezoidally embodied rest part 16 which is arranged on the neck part 12 by means of a flat hook-and-loop fastener 26a and 26b. Unsupported positioning of the neck 44 may thus be avoided in any position and during any movement of the patient. In particular, it is in this way possible to bring the head and the neck of the patient into a stable position which is suitable for the treatment, for example for intubating.

As illustrated in FIGS. 7 and 8, the rest 16 for the neck part 12 is also equipped with a tube 56 to be guided through an opening 13 in the support 2, a three-way valve 58 and a hand pump arrangement 60, so that the rest part 16 for the head part 12 can be adapted, before, during and after an operation, to the requirements, in particular the desired position and form of treatment.

Figure 13:
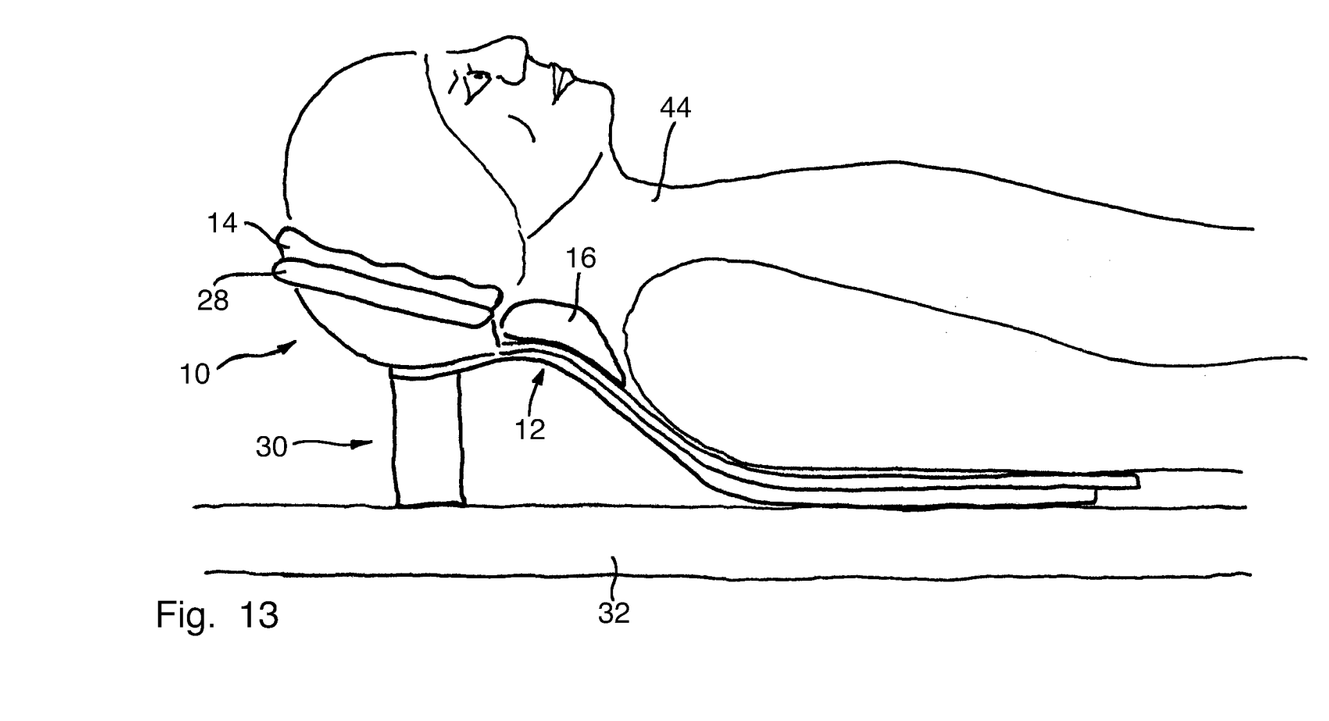
FIG. 13 is an illustration of the support, placed onto the operating table, with the head part placed on a support part.

Should the head part 10 not be connected to the corresponding adjustable head holding part 36 of the operating table 32, it is possible to provide a support device 30 which is used to support the head part 10 in such a way that the support 2 can be placed on a surface without the risk of tipping.

FIGS. 9 to 12 show modifications of the embodiment described hereinbefore. The support shown in FIG. 9 has, at a specific distance from the lateral edges of the body part 6, in each case slotted recesses 20 which each serve to fasten a belt half of a safety belt 22 which can be used to buckle the patient, who is positioned on the support 2, to the support 2. One or more support plates 23 are preferably arranged on the safety belt 22 to distribute the holding force of the safety belt in a flat manner on the patient's body. In principle, it is thus possible for the patient to be brought along with the support, mounted on the operating table 32, further into a beach chair position and into a sitting-up position. Furthermore, the patient can be detached from the operating table and repositioned by means of the support, or even transported independently thereof.

Figures 9, 10, 11:
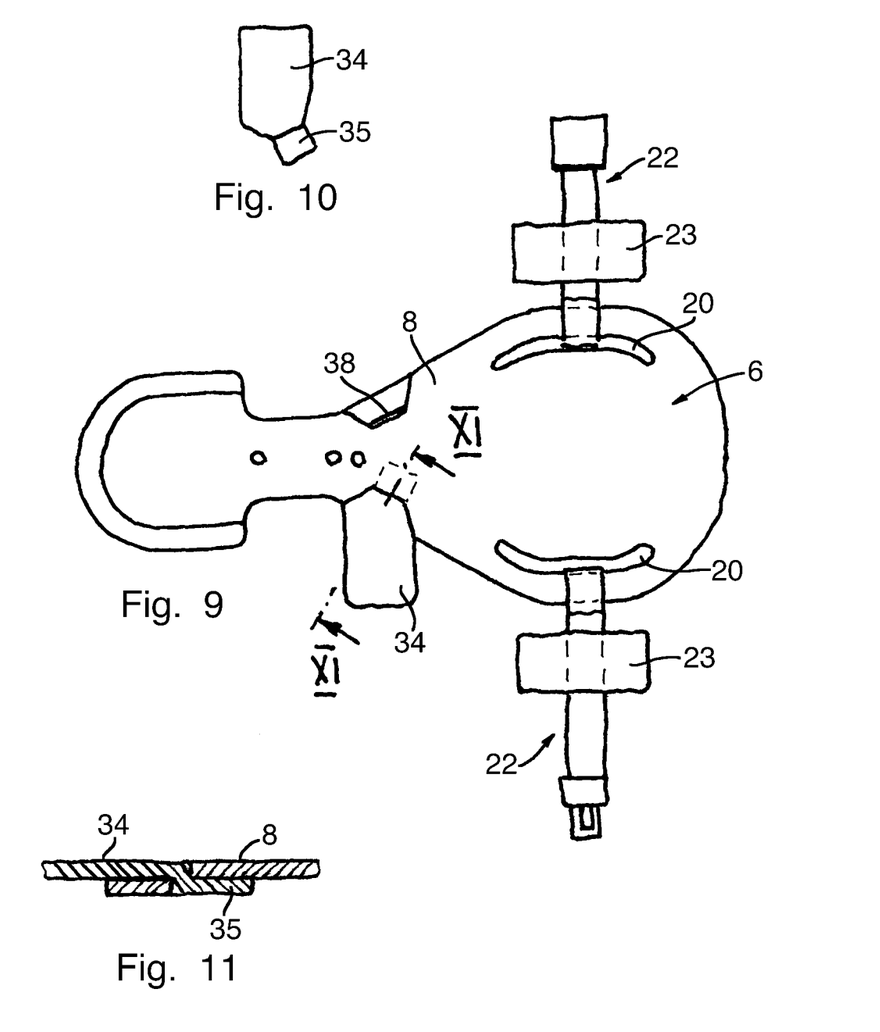
FIG. 9 is a plan view of a further support embodied in one piece according to a second exemplary embodiment of the present invention.
FIG. 10 shows a detachable support element for the shoulder region for the support according to FIG. 9.
FIG. 11 is a section XI-XI of the connecting region between the support element and the shoulder region of the support according to FIG. 10.
Figure 12:
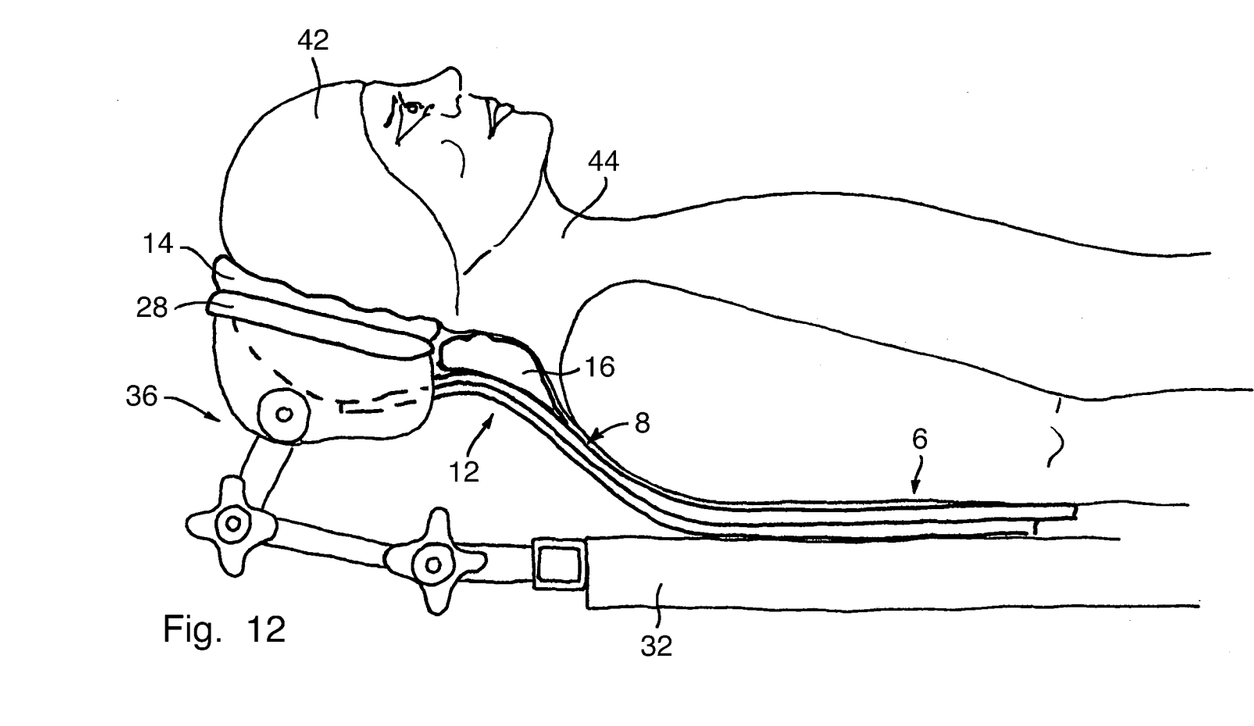
FIG. 12 is an illustration of the support, placed onto the operating table, with the head part clicked-in and a patient (indicated)

The thorax part 8 has on each side receiving slots 38 for the engaging of tongues 35 of support elements 34, such as is shown in particular in FIGS. 9 to 11. The detachable support elements 34 serve to form if necessary, for example when drilling in the shoulder region of the patient, an adequate mating surface. They are detachable, for the sake of dorsal access to the joint, when there is no need to ensure or to increase the possibility of moving the patient. The support elements are inserted and—as shown in FIG. 11—locked into the thorax part.

If appropriate, the head part 10 may not be embodied in one piece with the body part 4 and the neck part 12, but rather mounted thereon, for example detachably screwed thereto. This facilitates, for example, the exchange of the head part 10 when different-sized patients, for example children or youths, are to be operated on.

The support is used in operations, in particular in shoulder operations in what is known as the beach chair position. In this case, it is advantageous if tests with x-rays can be carried out during the operation or else before or after the operation, while the patient is still buckled to the support. For this reason, the support, in particular the head part 10, the neck part 12 and the body part 14, is made of a plastics material which is transparent to x-rays.

In the present exemplary embodiment, the support 2 is made of plastics material. In order to impart increased strength to the support, in particular to protect it from warping and torsion, the body part 4 and the neck part 12 of the support 2 are equipped on the back with a reinforcement rail 18.

A typical use of the support according to the invention will be described hereinafter. When the patient, who is positioned on and buckled to the support, is operated on, he is first given a soporific. He is therefore sleeping and is ventilated. As the cervical and thoracic spine are not supported, they would fall backward without an aid. The support according to the foregoing description allows the neck to be stabilized; as a result, it does not fall backward and, with the inflating of the trapezoidal rest 16, the neck can be pressed forward as desired, so that the head is automatically tilted back.

The support can be used in a broad range of applications; in each case, it ensures optimum supporting of the patient from the head via the neck and the shoulder and chest part up to the back. This is especially important in particular in the case of anesthesia, as the muscles of the patient are then relaxed and the body could sag at non-supported points and become damaged.

When transferring a patient to the operating table, i.e. before he is placed under anesthetic, it is noted in which position and at what level of pressure of the inflatable rests 14 and 16 he is comfortable and the rests and 16 are inflated accordingly. In addition, after a change in position, for example intubation, it would also be checked if the appropriate support by the neck part 12 and its rest 16 is missing.

For intubating, i.e. for introducing a tube into the windpipe of a patient, it may be necessary for the head also to be pressed forward in order to assume what is known as a sniffing or Jackson position. For this purpose, the annular rest 14 continues to be inflated. After intubation, the air is let out of this rest 14 back to a level determined beforehand by the patient.

When the patient—after intubation—is to be positioned, there is the risk, in conventional equipment, that the head part will shift. This is prevented by the mechanism for locking the projection 28 into the head holding part of the operating table 36. The head part 10 cannot slip out. Safety is further increased by the reinforcement rail which rigidifies the support 2—in the exemplary embodiment including the neck part 12.

list of reference numerals
2 Support
4 Body part
6 Back part
8 Thorax part
10 Head part
11 Opening
12 Neck part
13 Opening
14 Rest, head part
16 Rest, neck part
18 Reinforcement rail
20 Slotted recesses for receiving a safety belt
22 Safety belt
23 Support plate
24a, b Hook-and-loop fastener, head part
26a, b Hook-and-loop fastener, neck part
28 Projection, head part
30 Support device, head part
32 Operating table
34 Detachable support elements
35 Tab
36 Head holding part of the operating table
38 Incisions for receiving the support elements
40 Body
42 Head
44 Neck
50 Tube
52 Three-way valve
54 Hand pump arrangement
56 Tube
58 Three-way valve
60 Hand pump arrangement

The invention claimed is:

1. A support (2) configured for removable mounting on an operating table for supporting a patient resting on the operating table, said support comprising:
   a body part (4) having a substantially flat back part (6) corresponding to a location of the patient's middle back and having a thorax part (8) corresponding to a location of the patient's shoulder region, said thorax part (8) angled upward and rising from, and tapering width-wise in relation to, said back part (6), thereby exposing a dorsal portion of the patient's shoulder region; and a bowl-shaped head part (10) being adapted to the human profile and having a detachable, inflatable rest (14) for adapting the position of the patient to positional or treatment requirements, said head part being arranged on the thorax part (8) by means of a transitional region rising from and narrowed width-wise in relation to said thorax part (8)

in such a way that the head part (10) is higher than the back part (6);

the transitional region being embodied as a neck part (12) and being also adapted to the human profile with a detachable, inflatable rest (16) for adapting the position of the patient to the positional or treatment requirements.

2. The support as claimed in claim 1, characterized in that the head part (10) has means for connecting to an operating table.

3. The support as claimed in claim 2, characterized in that the means for connecting the head part (10) to the operating table are embodied as a projection (28) which encircles at least in certain pieces and can be locked into a corresponding counterpiece embodied or arranged on the operating table.

4. The support as claimed in claim 1, characterized in that the neck part (12) corresponds in its length at least to the length of the human neck (44) and in its width at least to half the width of the human neck (44).

5. The support as claimed in claim 1, characterized in that the body part (4) is adapted to the human profile.

6. The support as claimed in claim 1, characterized in that at least the body part (4) and the neck part (12) are embodied in one piece.

7. The support as claimed in claim 1, characterized in that the support (2) has on the back a reinforcement rail (18) extending substantially in the longitudinal center line.

8. The support as claimed in claim 1, characterized in that the body part (4) has in each of its lateral regions an elongate, slotted recess (20) for fastening a respective belt part of a safety belt (22).

9. The support as claimed in claim 1, characterized in that it has a support device (30), which can be attached or detached below the head part (10), for supporting the head part on an operating table.

10. The support as claimed in claim 1, characterized in that it has support elements (34) which can be attached or detached in the region of the thorax part (8) at both sides, in particular for the shoulder region of the patient.

11. The support as claimed in claim 1, characterized in that the inflatable rest (14) of the head part (10) is embodied in an annular manner.

12. The support as claimed in claim 1, characterized in that the inflatable rest (16) of the neck part (12) is embodied in a substantially trapezoidal manner.

13. The support as claimed in claim 1, characterized in that the detachable, inflatable rest (14) of the head part (10) and/or the detachable, inflatable rest (16) of the neck part (12) has a hook-and-loop fastener which can be used to arrange the rest on the head part (10) or on the neck part (12).

14. The support as claimed in claim 1, characterized in that the head part (10), the neck part (12) and the body part (4) are made predominantly of a plastics material which is transparent to x-rays.

\* \* \* \* \*